United States Patent
Cravaack et al.

(10) Patent No.: US 6,974,361 B2
(45) Date of Patent: Dec. 13, 2005

(54) APPARATUS FOR SUPPORTING MILK EXTRACTION DEVICES

(76) Inventors: Traci Cravaack, 8825 Stratford Crossing, Brooklyn Park, MN (US) 55443; Catherine Luciano, 2413 NW. 49th La., Boca Raton, FL (US) 33431; Laurie Zanotti, W293 N6728 Cheryl La., Hartland, WI (US) 53029

(*) Notice: Subject to any disclaimer, the term of this patent is extended or adjusted under 35 U.S.C. 154(b) by 0 days.

(21) Appl. No.: 09/920,472

(22) Filed: Aug. 1, 2001

(65) Prior Publication Data

US 2003/0027491 A1 Feb. 6, 2003

(51) Int. Cl.⁷ .................................................. A41C 3/00
(52) U.S. Cl. .......................................... 450/36; 450/37
(58) Field of Search .......................... 450/36–37, 7–10, 450/15–18, 65–67, 79, 82; 2/104, 114, 115; 604/73–76, 118–119

(56) References Cited

U.S. PATENT DOCUMENTS

| | | | | |
|---|---|---|---|---|
| 1,189,589 A | * | 7/1916 | Lawrence | 450/36 |
| 5,575,768 A | * | 11/1996 | Lockridge et al. | 604/74 |
| 6,004,186 A | * | 12/1999 | Penny | 450/36 |
| 6,213,840 B1 | * | 4/2001 | Han | 450/36 |
| 6,227,936 B1 | * | 5/2001 | Mendoza | 450/36 |
| 6,247,996 B1 | * | 6/2001 | Fields | 450/36 |

* cited by examiner

Primary Examiner—Gloria M. Hale
(74) Attorney, Agent, or Firm—Lisa A. Brzycki; Gehrke & Associates, S.C.

(57) ABSTRACT

An apparatus for supporting milk extraction devices includes an elongated elastic strap that is adjusted to frictionally engage a woman's breasts. A pair of slits is formed in the elastic strip and each of the slits is positioned proximate the woman's breasts. The slits support the milk extraction devices therethrough. Each of the slits is a collapsible opening that alternates between a closed position when the milk extraction device is not supported by the slit and a partially opened position when the milk extraction device is supported by the slit.

11 Claims, 6 Drawing Sheets

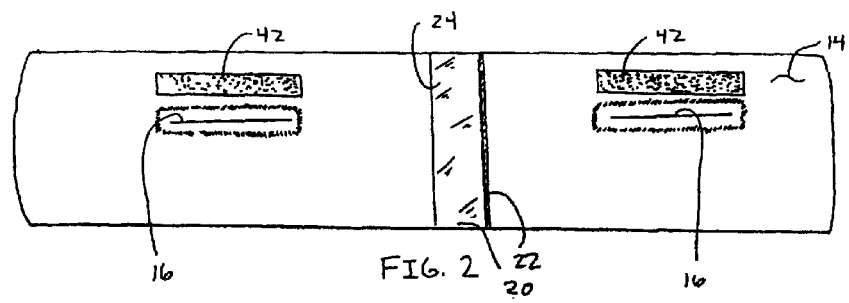
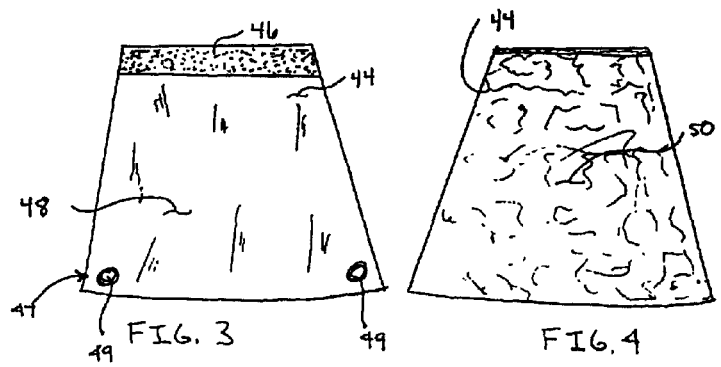
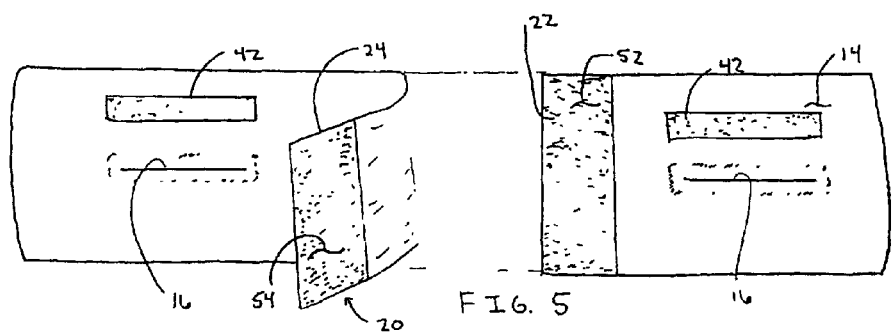

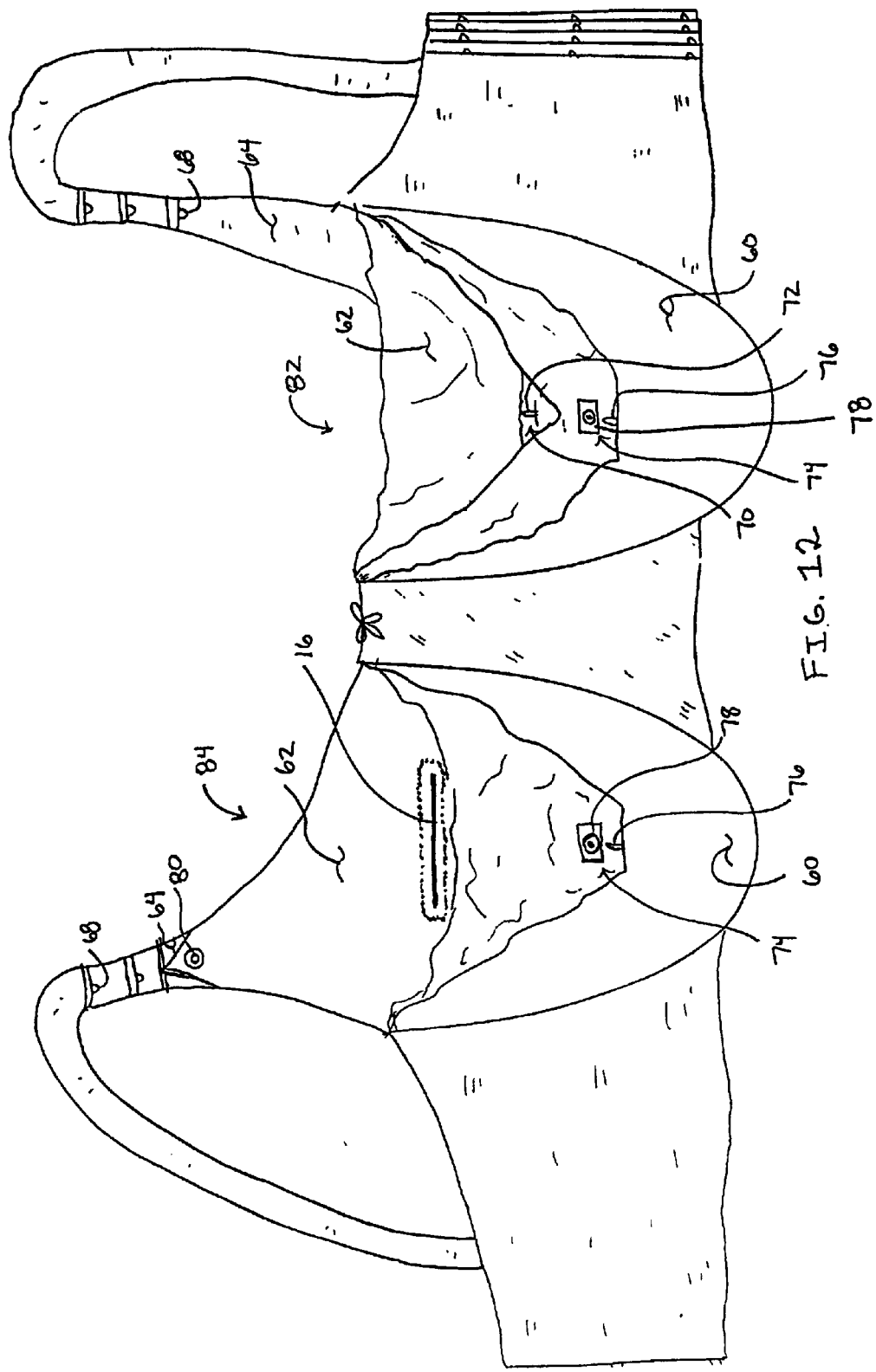

APPARATUS FOR SUPPORTING MILK EXTRACTION DEVICES

BACKGROUND OF THE INVENTION

1. Field of the Invention

This invention is in the field of breastfeeding, specifically relating to an apparatus fitted around a woman's breasts to aid in the mechanical extraction of breast milk using one or multiple milk extraction suction devices.

2. Description of the Related Art

For the sake of convenience, this patent specification will focus on simultaneously pumping both breasts using two separate milk extraction devices, but it is understood that the problems addressed and solutions presented by the present invention are also applicable to extracting milk using a single milk extraction device (e.g., nursing a baby on one breast while simultaneously pumping the other breast) or pumping each breast separately.

A breast pump includes suction cup devices that are secured to the nipples of the mother's breasts. Tubes connect the suction devices to the breast pump and a motor in the pump typically creates varying degrees of suction between the suction devices and the breasts. The suction extracts breast milk from the breasts into a pair of bottles attached to the suction devices. The mother maintains the suction by manually pressing the suction devices against the breasts throughout the pumping procedure. This is often a time consuming and frustrating process as the mother must maintain a particular position for a long period of time without any use of her hands.

Despite this frustration, it has become increasingly common for working mothers to choose to maintain a breast-feeding relationship with their child by using electric, battery or manual breast pumps to extract milk several times a day while at work. While the breast pumps are able to extract milk, they still are not nearly as efficient as a nursing baby. Therefore, several companies have set up separate rooms and policies to help nursing mothers maintain the breast-feeding relationship with their child. In this regard, one of the keys to maintaining a breastfeeding relationship is the ability of the nursing mother to relax and quickly experience the let-down reflex. This is difficult to achieve while concentrating on maintaining proper suction by using both hands to press each of the suction devices against the breasts.

Additionally, nursing mothers often find themselves in situations where they have to pump in front of other people. In this regard, it would be useful to provide the nursing mother with a means to cover her breasts while she is pumping. It would also be useful to provide the nursing mother with a pumping device that is easily adjusted in the front for easy access.

A device that would allow a breastfeeding mother to have full use of her hands during each of the pumping sessions would allow the mother to relax and even perform other tasks while pumping. It is critical that such a device be capable of providing adequate pressure between the suction device and the breasts to adequately and efficiently empty the breasts. Unfortunately, current devices adapted to allow a nursing mother "hands free" pumping simply do not work, as they are unable to maintain proper suction between the suction devices and the breasts.

Moreover, several of these devices require the assembly and disassembly of several complicated attachments to hold the suction devices in place. These devices are typically very expensive and still ineffective at maintaining the proper suction between the devices and the breasts, thereby allowing hands free pumping. Finally, these devices also may require permanent alteration of the nursing brassiere, thereby rendering it ineffective for nursing the baby in that after the attachments are secured to the brassiere, the brassiere can only be used as a pumping aid.

SUMMARY OF THE INVENTION

Accordingly, one object of this invention is to provide an apparatus for supporting milk extraction devices including an elongated elastic strap that is adjusted to frictionally engage a woman's breasts. A pair of slits is formed in the elastic strip and each of the slits is positioned proximate the woman's breasts. The slits support a milk extraction device therethrough. Each of the slits is a collapsible opening that alternates between a closed position when the milk extraction device is not supported by the slit and a partially opened position when the milk extraction device is supported by the slit.

Another object of this invention is to provide an apparatus for supporting milk extraction devices including an elongated elastic strap that is adjusted to frictionally engage a woman's breasts. A pair of collapsible openings is formed in the elastic strip and positioned proximate the woman's breasts. The pair of collapsible openings supports the milk extraction device therethrough. The milk extraction device includes a circular suction cup and the elongated elastic strip substantially covers the majority of the surface area of the circular suction cup when the suction cup is inserted into the collapsible opening.

Yet another object of this invention is to provide a nursing/pumping brassiere including front panel, a middle panel and a rear panel. The front panel supports a woman's breast and the middle panel is partially attached to the front panel. The middle panel includes a slit formed therein and positioned proximate the woman's breast. The slit supports a milk extraction device therethrough and alternates between a closed position when the milk extraction device is not supported by the slit and a partially opened position when the milk extraction device is supported by the slit. The rear panel is adjacent to the woman's breast and includes attachment means for supporting the middle panel.

BRIEF DESCRIPTION OF THE DRAWINGS

Preferred exemplary embodiments of the invention are illustrated in the accompanying drawings in which like reference numerals represent like parts throughout, and in which:

FIG. 2 is a front view of the apparatus according to the present invention;

FIG. 3 is a rear view of a privacy flap according to the present invention;

FIG. 4 is a front view of the privacy flap according to the present invention;

FIG. 5 is a front view of the apparatus in an opened position according to the present invention;

FIG. 12 is a front view of the nursing/pumping brassiere illustrating the back panel, the middle panel having the slit, and a front panel according to the present invention.

DETAILED DESCRIPTION OF THE PREFERRED EMBODIMENTS

Figure 1:
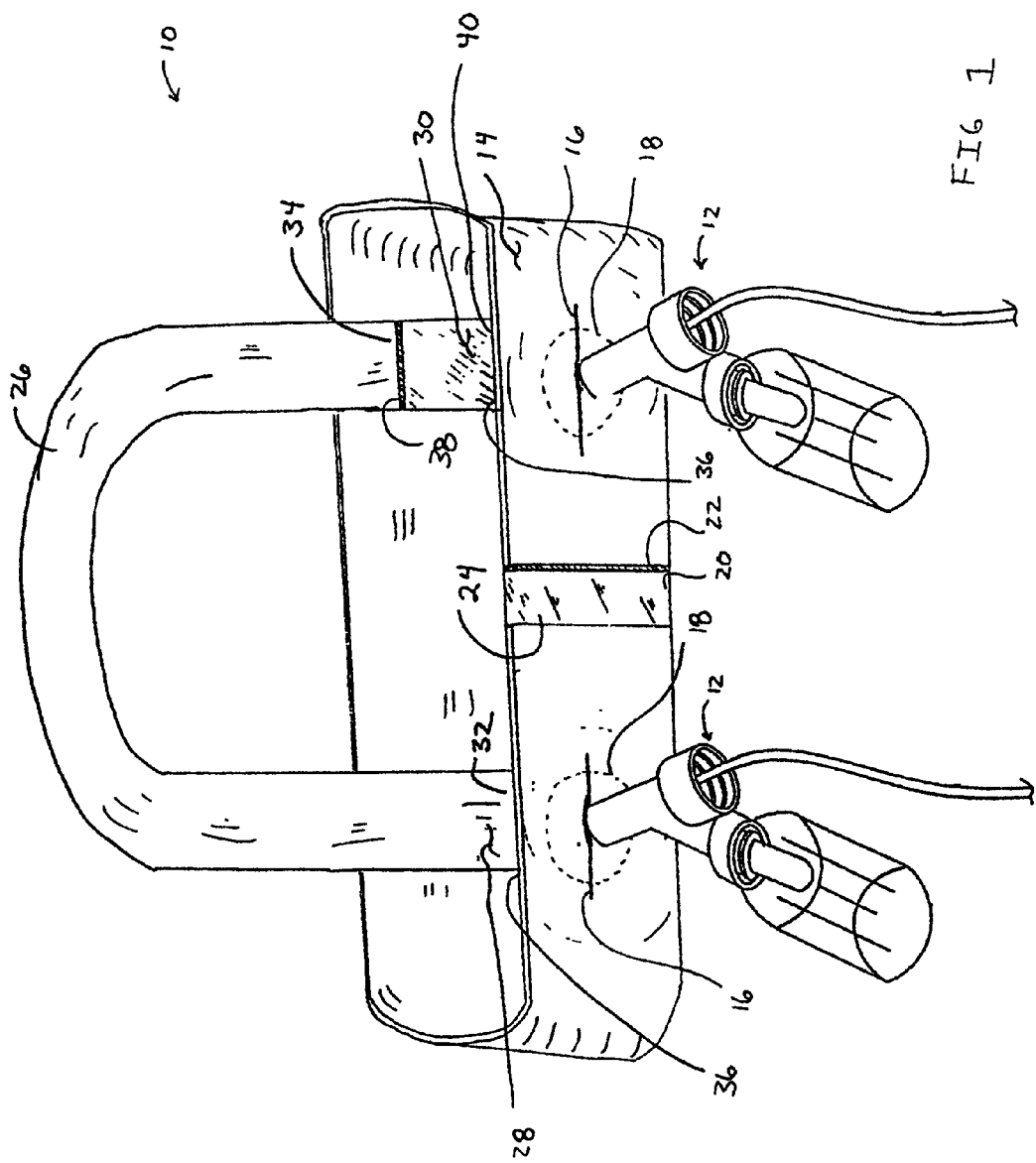
FIG. 1 is a perspective view of a halter apparatus according to the present invention.

Referring to FIG. 1, an apparatus 10 for supporting a pair of milk extraction devices 12 includes an elongated strap 14 that is adjusted to frictionally engage and wrap around a nursing mother's breasts. A pair of slits 16 is formed in elongated strap 14 and each of the slits is aligned with the nipple portion of each breast. Slits 16 support a circular suction cup 18 (dotted lines) of milk extraction device 12. In the preferred embodiment of the current invention, each slit is approximately 3–6 inches in length (e.g., 4½ inches). Elongated strap 14 is approximately 33 inches (small), 35 inches (medium), 37 inches (large), 40 inches (extra large), or 45 inches (XX large).

Each slit 16 is a button-hole type of collapsible opening that alternates between a closed position when milk extraction devices 12 are not supported by slits 16 and a partially opened position when milk extraction devices 12 are supported by slits 16.

In the preferred embodiment of the current invention, strap 14 is constructed by covering an elastic-type band (e.g., 3 to 10 inches in width) with a stretchable material (e.g., Lycra®, Spandex®, etc.). Alternatively, strap 14 may be manufactured with a non-stretchable woven or non-woven material (e.g., terry cloth, rayon, polyester, etc.).

Strap 14 is configured to adapt to varying chest and cup sizes with a temporary closure means 20 known in the art (e.g., Velcro® hook and loop fastener closures, button and button holes, hook and eye closures, snaps, tied fabric extensions, etc.). In the preferred embodiment of the current invention, a first end 22 of strap 14 is removably attached to a second end 24 of strap 14 using mating strips of Velcro® located in front of the nursing mother. In the alternative, strap 14 may be manufactured to accommodate varying chest and cup sizes consistent with industry standards (e.g., small, medium, large, extra-large) or custom fit.

Temporary closure means 20 is used to adjust the friction between elongated elongated strap 14 and the woman's breasts. As illustrated in FIG. 1, closure 20 is located between slits 16 to provide easy adjustment of strap 14 for adequate friction to support milk extraction devices 12 and to align slits 16 with the woman's breasts.

In an alternative embodiment of the current invention, strap 14 may be manufactured as a single tubular shape having permanently secured ends to form a continuous piece of fabric. The ends may be secured with methods that are well-known in the art (e.g., heat-activated fusible material, fabric adhesive, thread, etc.).

Apparatus 10 further includes a halter-type neck strap 26 with a first strap portion 28 and a second strap portion 30. First strap portion 28 further includes a first end 32 and a second end 34. First end 32 of first strap portion 28 is attached to elongated strap 14 proximate one of slits 16.

Halter-type neck strap 26 is constructed by covering an elastic-type band (e.g., 1 to 3 inches in width) with a stretchable material (e.g., Lycra®, Spandex®, etc.). Alternatively, neck strap 26 may be manufactured with a non-stretchable woven or non-woven material (e.g., terry cloth, rayon, polyester, etc.). Neck strap 26 is approximately 25 to 35 inches in length.

In the preferred embodiment of the present invention, first end 32 of first strap portion 28 is permanently attached to elongated strap 14 at a top portion 36 of elongated strap 14. Second end 34 of first strap portion 28 is temporarily attached to a first end 38 of second strap portion 30 using adjusting means (e.g., mating strips of Velcro® attached to second end 34 and first end 38). A second end 40 of second strap portion 30 is permanently attached to elongated strap 14 at top portion 36 of elongated strap 14 proximate one of slits 16.

Alternatively, one or both of first end 32 of first strap portion 28 and second end 40 of second strap portion 30 may be temporarily attached to top portion 36 of elongated strap 14 using adjusting means that are well-known in the art (e.g., mating Velcro® strips).

In yet another alternative embodiment of the present invention, neck strap 26 may be manufactured from a single piece of material that having two ends that are attached to top portion 36 proximate each of slits 16 either permanently or temporarily (e.g., using a Velcro®-type closure). In the preferred and alternative configurations, neck strap 26 wraps behind the neck and is adjusted using adjusting means located in front of the nursing mother.

In operation, a nursing mother wraps elongated elastic strap 14 around her chest, aligns slits 16 with her breasts, and obtains a tight fit using closure means 20. To provide further comfort, the nursing mother may also place neck strap 26 behind her neck and adjust the position of strap 26 by changing the position of second end 34 in relation to first end 38.

Circular suction cups 18 of milk extraction devices 12 are inserted through slits 16 and elongated strap 14 may be adjusted to ensure proper friction between cups 18 and the woman's breasts. Thereafter, the nursing mother turns on the breast pump and is able to maintain a comfortable position while extracting milk and having full use of both of her hands. At the end of the pumping session, the nursing mother turns off the breast pump, easily removes cups 18 from slits 16, and removes elongated strap 14 from her breasts.

FIG. 2 illustrates elongated strap 14 having button-hole type slits 16 and temporary attachment means 42 located directly above slits 16. Temporary attachment means 42 supports a pair of privacy flaps 44 (FIGS. 3 and 4) configured to partially cover milk extraction devices 12. In the preferred embodiment of the current invention, attachment means 42 is a Velcro® strip that mates with a corresponding Velcro® strip 46 located on a rear side 48 of privacy flap 44 (FIG. 3). Strip 46 aligns with strip 42 and rear side 48 of flap 44 is adjacent to milk extraction device 12. A front side 50 of privacy flap 44 is manufactured from a patterned or nonpatterned material to distract attention away from suction cups 18.

As illustrated in FIG. 3, privacy flaps 44 further include closure means 47 including a pair of mating Velcro® tabs 49. Prior to beginning a pumping session, the nursing mother secures privacy flaps 44 to elongated strap 14 above slits 16 and then wraps each privacy flap 44 around each milk extraction device 12 using tabs 49. In this position, privacy flaps 44 completely cover the nipple area as the nursing mother extracts milk.

FIG. 5 illustrates closure means 20 including first end 22 of elongated strap 14 having a Velcro® strap 52 that mates with a Velcro® strap 54 on second end 24 of elongated strap 14.

Figure 6:
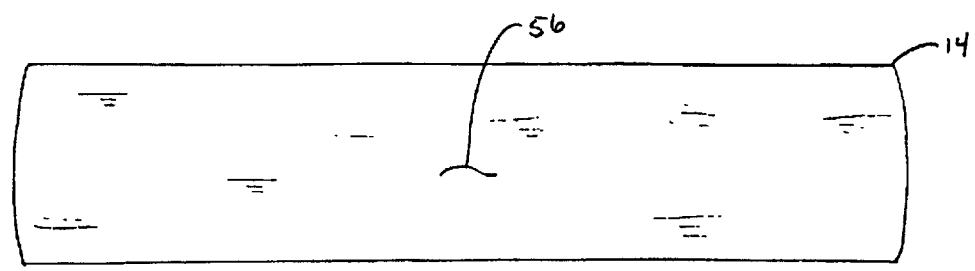
FIG. 6 is a rear view of the apparatus according to the present invention.
Figure 7:
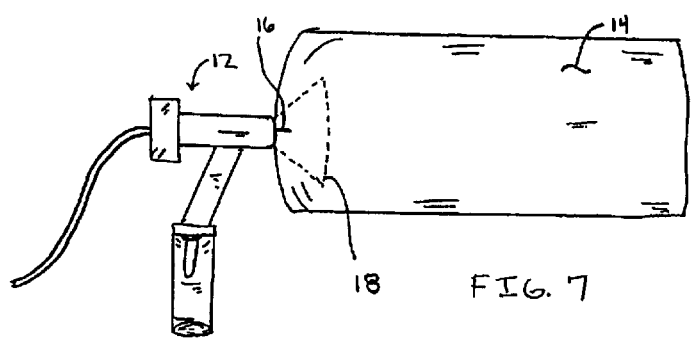
FIG. 7 is a side view of the apparatus according to the present invention.

FIG. 6 illustrates a rear side 56 of elongated strap 14 and FIG. 7 illustrates a side view of elongated strap 14 including suction cup 18 of milk extraction device 12 inserted through slit 16.

Figure 8:
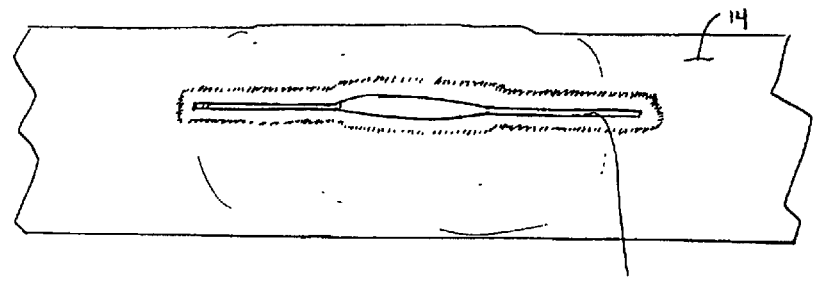
FIG. 8 is a front view of a partially opened slit in the apparatus according to the present invention.

FIG. 8 illustrates slit 16 in a partially open position when suction cup 18 (not shown) is inserted through slit 16. Slit 16 maintains a substantially closed position even with the insertion of suction cup 18, thereby maintaining a frictional engagement between elongated strap 14 and the nursing mother's breasts and providing adequate support for milk extraction devices 12. Moreover, the majority of the surface area of circular suction cup 18 is substantially covered by elongated strap 14 because slit 16 is a collapsible-type opening.

Figure 9:
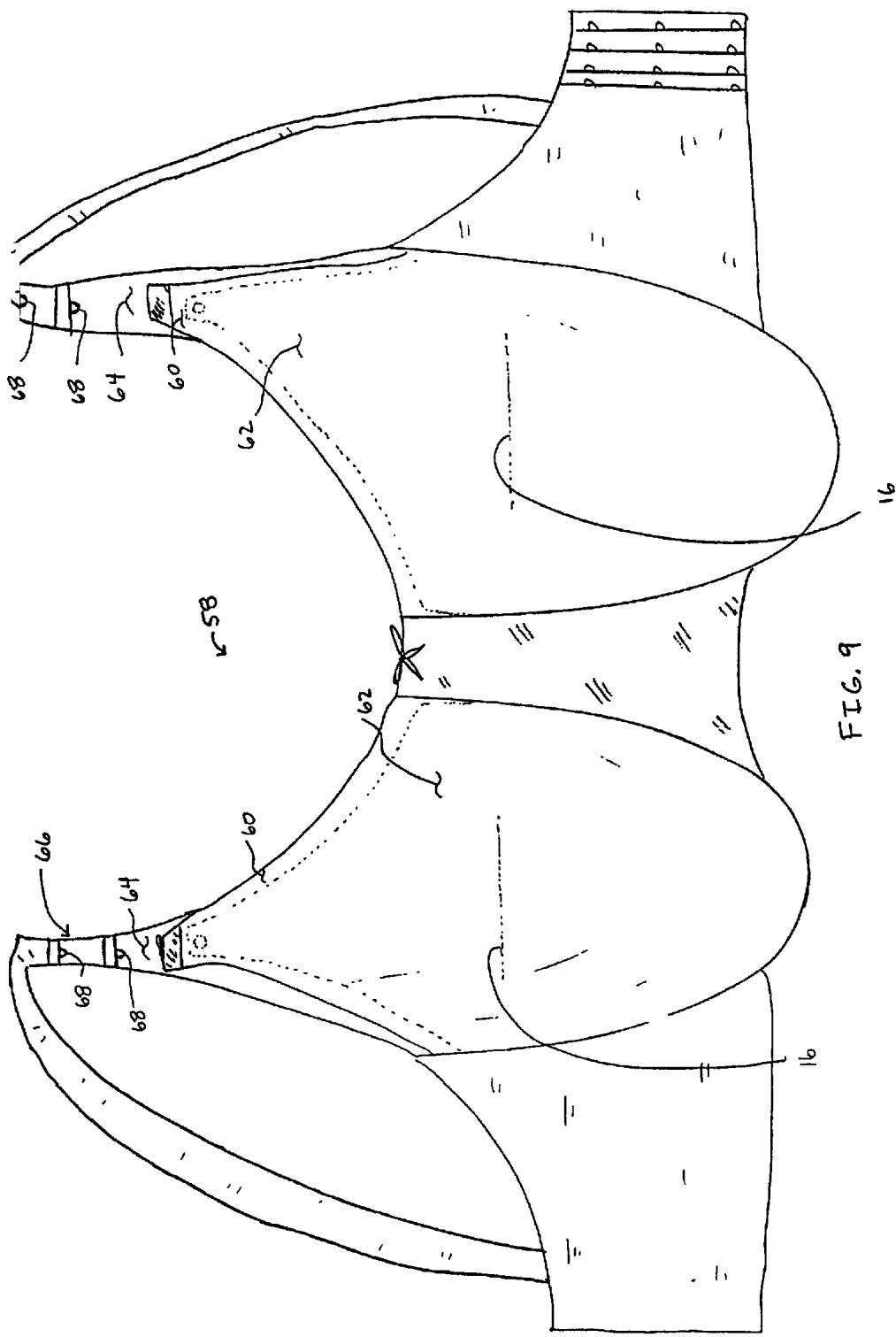
FIG. 9 is a front view of a nursing/pumping brassiere according to the present invention.
Figure 10:
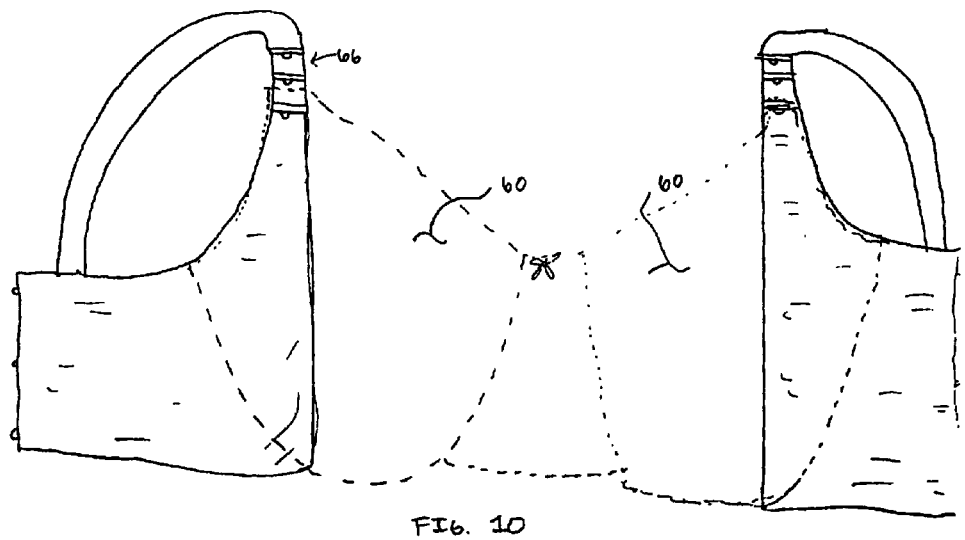
FIG. 10 is a partial front view of the nursing/pumping brassiere illustrating a back panel according to the present invention.
Figure 11:
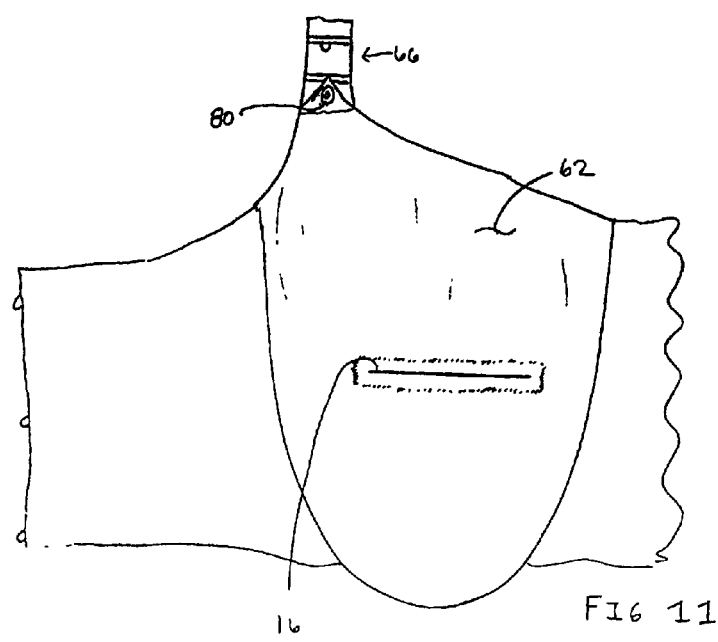
FIG. 11 is a partial front view of the nursing/pumping brassiere illustrating a middle panel including a slit to support the milk extraction devices according to the present invention.

In an alternative embodiment of the present invention illustrated in FIG. 9, a combination nursing/pumping brassiere 58 is used as both a pumping device to support milk extraction devices 12 and as a nursing bra. Brassiere 58 includes a front panel 60 to support a woman's breast, a middle pumping panel 62 (dotted lines) located behind and partially attached to front nursing panel 60, and a rear panel 64.

Middle panel 62 includes slit 16 that supports milk extraction device 12 and alternates between a closed position when milk extraction device 12 is not supported by slit 16 and a partially opened position when milk extraction device 12 is supported by slit 16.

Rear panel 64 includes attachment means 66 such as a series of staggered eyes 68. Middle panel 62 similarly includes attachment means 70 (FIG. 12) such as a hook 72 that is inserted through one of eyes 68 to support middle panel 62. Front panel 60 also includes attachment means 74 such as a hook 76 that is inserted through one of eyes 68 to support front panel 60. In the preferred embodiment of the present invention, attachment means 74 further includes a snap 78 that engages a counterpart snap portion 80 attached to middle panel 62.

In operation, middle panel 62 is attached to front panel 60 with snap 78 engaging snap portion 80, and front panel 60 is secured to rear panel 64 by inserting hook 76 into one of eyes 68. If a nursing mother is going to nurse a baby, the nursing mother removes hook 76 from one of eyes 68 and folds front panel 60 and middle panel 62 forward into a fully opened position 82 to expose the breast.

If a nursing mother is going to use milk extraction devices 12, the nursing mother removes hook 76 from one of eyes 68, unsnaps snap 78 from engagement with snap portion 80, folds down front panel 60 to expose slit 16, and engages hook 72 with one of eyes 68 to place nursing/pumping brassiere 58 into a pumping position 84.

In an alternative embodiment of nursing/pumping brassiere 58, front panel 60 is not attached to middle panel 62 so that both front panel 60 and middle panel 62 are independently supported using attachment means 66 located on rear panel 64.

Many changes and modifications may be made to the invention without departing from the spirit thereof. The scope of some of these changes has already been discussed in relation to using other attachment and adjusting means for fastening various portions of elongated strap 14 and nursing/pumping brassiere 58 to one another (e.g., replacing snaps 78 and 80 with Velcro®, etc.). The scope of other changes will become apparent from the attached claims.

What is claimed is:

1. An apparatus for supporting milk extraction devices comprising:
   an elongated elastic strap that is adjusted to frictionally engage a woman's breasts;
   a pair of horizontal slits formed in the elastic strip, wherein each of the slits is positioned proximate the woman's breasts and configured to support a milk extraction device therethrough;
   a pair of privacy flaps attached above each of the slits and configured to partially cover the milk extraction devices, wherein the flaps are removably attached to the elastic strap and
   wherein each of the slits is a collapsible opening that alternates between a closed position when the milk extraction device is not supported by the slit and a partially opened position when the milk extraction device is supported by the slit.

2. The apparatus according to claim 1, wherein the milk extraction device includes a circular suction device and the elongated elastic strip substantially covers the majority of the surface area of the circular suction device after the suction device is inserted into the slit.

3. The apparatus according to claim 1, further comprising a neck strap having a first portion and a second portion, wherein a first end of the first portion and a second end of the second portion are attached proximate each of the slits in the elastic strap, and a second end of the first portion is attached to a first end of the second portion.

4. The apparatus according to claim 3, wherein the first end of the first portion of the neck strap and the second end of the second portion of the neck strap are permanently attached to the elastic strap and the second end of the first portion is temporarily attached to the first end of the second portion.

5. The apparatus according to claim 1, wherein the elastic strap further includes temporary closure means to adjust the friction between the elastic strap and the woman's breasts.

6. The apparatus according to claim 5, wherein the temporary closure means is located between the pair of slits.

7. An apparatus for supporting milk extraction devices comprising:
   an elongated elastic strap that is adjusted to frictionally engage a woman's breasts;
   a pair of horizontal collapsible openings formed in the elastic strip, wherein each of the collapsible openings is positioned proximate the woman's breasts and configured to support a milk extraction device therethrough;
   a pair of privacy flaps attached above each of the slits and configured to partially cover the milk extraction devices, wherein the flaps are removably attached to the elastic strap and
   wherein the milk extraction device includes a circular suction cup and the elongated elastic strip substantially covers the majority of the surface area of the circular suction cup when the suction cup is inserted into the collapsible opening.

8. The apparatus according to claim 7, further comprising a neck strap having a first portion and a second portion, wherein a first end of first portion and a second end of the second portion are attached proximate each of the collapsible openings in the elastic strap, and a second end of the first portion is attached to a first end of the second portion.

9. The apparatus according to claim 8, wherein the first end of the first portion of the neck strap and the second end of the second portion of the neck strap are permanently attached to the elastic strap and the second end of the first portion is temporarily attached to the first end of the second portion.

10. The apparatus according to claim 9, wherein the elastic strap further includes temporary closure means to adjust the friction between the elastic strap and the woman's breasts.

11. The apparatus according to claim 10, wherein the temporary closure means is located between the pair of slits.

* * * * *